United States Patent
May et al.

(10) Patent No.: US 11,905,239 B2
(45) Date of Patent: Feb. 20, 2024

(54) PROCESS FOR PRODUCING METHACRYLIC ACID OR METHACRYLIC ACID ESTERS

(71) Applicant: Röhm GmbH, Darmstadt (DE)

(72) Inventors: Alexander May, Seeheim-Jugenheim (DE); Steffen Krill, Muehltal (DE); Marcel Treskow, Mobile, AL (US); Diego Carambia, Jose C. Paz (AR); Gabriel Avella, San Isidro (AR)

(73) Assignee: Röhm GmbH, Darmstadt (DE)

( * ) Notice: Subject to any disclaimer, the term of this patent is extended or adjusted under 35 U.S.C. 154(b) by 0 days.

(21) Appl. No.: 18/056,338

(22) Filed: Nov. 17, 2022

(65) Prior Publication Data
US 2023/0080750 A1    Mar. 16, 2023

Related U.S. Application Data

(62) Division of application No. 17/266,735, filed as application No. PCT/EP2019/068644 on Jul. 11, 2019.

(30) Foreign Application Priority Data

Aug. 10, 2018    (EP) .................................... 18188458

(51) Int. Cl.
| | | |
|---|---|---|
| C07C 67/39 | (2006.01) | |
| B01J 23/38 | (2006.01) | |
| B01J 35/02 | (2006.01) | |
| C07C 45/75 | (2006.01) | |
| C07C 45/83 | (2006.01) | |
| C07C 51/25 | (2006.01) | |
| B82Y 30/00 | (2011.01) | |
| B82Y 40/00 | (2011.01) | |

(52) U.S. Cl.
CPC ............... *C07C 67/39* (2013.01); *B01J 23/38* (2013.01); *B01J 35/023* (2013.01); *C07C 45/75* (2013.01); *C07C 45/83* (2013.01); *C07C 51/252* (2013.01); *B82Y 30/00* (2013.01); *B82Y 40/00* (2013.01)

(58) Field of Classification Search
CPC ......... B01J 23/38; B01J 35/023; B82Y 30/00; B82Y 40/00; C07C 45/62; C07C 45/75; C07C 45/83; C07C 47/02; C07C 47/22; C07C 51/252; C07C 57/04; C07C 67/39; C07C 69/54; H01M 8/1004; H01M 8/1055; H01M 8/1065; Y02E 60/50
See application file for complete search history.

(56) References Cited

U.S. PATENT DOCUMENTS

| | | | |
|---|---|---|---|
| 4,049,577 A * | 9/1977 | Childress | ................ C07C 45/35 502/178 |
| 5,969,178 A | 10/1999 | Okamoto et al. | |
| 6,680,405 B1 | 1/2004 | Munetou et al. | |
| 7,012,039 B2 | 3/2006 | Watanabe et al. | |
| 9,890,105 B2 | 2/2018 | Krill et al. | |
| 10,273,201 B2 | 4/2019 | Krill et al. | |
| 10,457,626 B2 | 10/2019 | Krill et al. | |
| 10,766,847 B2 | 9/2020 | Krill et al. | |
| 2003/0060655 A1* | 3/2003 | Hayashi | ................... B01J 23/52 502/343 |
| 2007/0021631 A1 | 1/2007 | Yada et al. | |
| 2009/0005614 A1 | 1/2009 | Hulteberg et al. | |
| 2011/0105789 A1 | 5/2011 | Miyatake et al. | |
| 2011/0301316 A1* | 12/2011 | Dubois | ................. C07C 51/252 560/208 |
| 2016/0068464 A1 | 3/2016 | Krill et al. | |
| 2017/0275227 A1 | 9/2017 | Burghardt et al. | |
| 2018/0050977 A1 | 2/2018 | Krill et al. | |
| 2019/0077742 A1 | 3/2019 | Krill et al. | |
| 2019/0084914 A1 | 3/2019 | Krill et al. | |
| 2019/0112255 A1 | 4/2019 | Krill et al. | |

FOREIGN PATENT DOCUMENTS

| | | |
|---|---|---|
| CN | 1572772 | 2/2005 |
| CN | 102659541 | * 9/2012 |
| GB | 497757 | 12/1938 |
| WO | 2012/072697 | 6/2012 |
| WO | 2014/170223 | 10/2014 |

OTHER PUBLICATIONS

CN102659541 translated (Year: 2012).*
Chemical Identifiers (published May 2010, one page) (Year: 2010).*
Lie et al. (The Canadian Journal of Chemical Engineering, vol. 95, pp. 1985-1992, Published Online Mar. 2017) (Year: 2017).*
Hoang-Van et al. (Studies of High surface area Pt/MoO3 and Pt/WO3 catalysts for selective hydrogenation reactions. II. Reactions of acrolein and allyl alcohol, Applied Catalysis A: General 164, pp. 91-103, Published 1997) (Year: 1997).*
International Search Report dated Oct. 8, 2019, in PCT/EP2019/068644.
Lie et al.,"Rapid and Continuous Synthesis of Methacrolein with High Selectivity by Condensation of Propanal with Formaldehyde in Laboratory" The Canadian Journal of Chemical Engineering, vol. 95, Oct. 2017, pp. 1985-1992.
Written Opinion dated Oct. 8, 2019, in PCT/EP2019/068644.

* cited by examiner

*Primary Examiner* — Yevgeny Valenrod
*Assistant Examiner* — Blaine G Doletski
(74) *Attorney, Agent, or Firm* — Grüneberg and Myers, PLLC

(57) ABSTRACT

A process can be used for producing methacrylic acid or a methacrylic acid ester. The process involves producing acrolein, reacting the produced acrolein with hydrogen to produce propanal, reacting the propanal with formaldehyde to produce methacrolein, and oxidizing the methacrolein in the presence of an oxygen containing gas and optionally an alcohol, to obtain methacrylic acid or methacrylic acid ester.

19 Claims, No Drawings

PROCESS FOR PRODUCING METHACRYLIC ACID OR METHACRYLIC ACID ESTERS

CROSS-REFERENCE TO RELATED APPLICATIONS

This application is a divisional application of U.S. Application Ser. No. 17/266,735, filed on Feb. 8, 2021, which was the National Stage entry under § 371 of International Application No. PCT/EP2019/068644, filed on Jul. 11, 2019, and which claims the benefit of priority to European Application No. 18188458.6, filed on Aug. 10, 2018. The content of each of these applications is hereby incorporated by reference in its entirety.

BACKGROUND OF THE INVENTION

Field of the Invention

The present invention relates to a process for producing methacrylic acid or methacrylic acid esters. The present invention is directed to a new process for the production of methacrylic acid or alkyl methacrylate starting from Acrolein, which is available from glycerol or propane.

Description of Related Art State f the Art

Methacrylic acid and methacrylic acid esters, such as methyl methacrylate (MMA) are used in a wide variety of applications. Methyl methacrylate is moreover an important building block for various specialty esters of methacrylic acid (MAA), these being produced by transesterification with the corresponding alcohol.

The commercial production of methacrylic acid occurs, among other ways, by heterogeneously catalyzed gas phase oxidation of isobutylene, tert-butanol, methacrolein or isobutyl aldehyde. The thus obtained, gaseous reaction phase is transformed into an aqueous methacrylic acid solution by cooling and condensing, optionally separated from low-boiling substances such as, for example, acetaldehyde, acetone, acetic acid, acrolein and methacrolein and then introduced into a solvent extraction column, in order to extract and separate methacrylic acid by means of suitable extraction agents, such as, for example, short-chain hydrocarbons. The separated methacrylic acid is further purified, for example by distillation, to separate high-boiling impurities, such as, for example, benzoic acid, maleic acid and terephthalic acid, in order to obtain a pure methacrylic acid. Such a known process is described for example in EP 0 710 643, U.S. Pat. Nos. 4,618,709, 4,956,493, EP 386 117 and U.S. Pat. No. 5,248,819.

Methyl methacrylate (MMA) is nowadays mostly produced from hydrogen cyanide and acetone by way of the resultant acetone cyanohydrin (ACH) as main intermediate. This process has the disadvantage of producing very large amounts of ammonium sulphate, treatment of which incurs very high costs. Other processes not based on ACH are described in the relevant patent literature and are also carried out on a production scale. Among the raw materials used in this context as starting materials are those based on C-4 compounds, for example isobutylene or tert-butanol, which are converted by way of a plurality of stages to the desired methacrylic acid derivatives.

The general procedure here is that isobutylene or tert-butanol is oxidized in a first stage to give methacrolein, which is then reacted with oxygen to give methacrylic acid. Methanol is then used to convert the resultant methacrylic acid to MMA. Further details of the said process are described inter alia in Ullmann's Encyclopedia of Industrial Chemistry 2012, Wiley-VCH Verlag GmbH & Co. KGaA, Weinheim, Methacrylic Acid and Derivatives, DOI: 10.1002/14356007.a16_441.pub2, and in Trends and Future of Monomer-MMA Technologies, SUMITOMO KAGAKU 2004-II.

Ethylene can also be used as starting material instead of a C4 building block such as isobutylene in one variant of said production method, and is first reacted with synthesis gas to give propanal; reaction with formaldehyde then gives methacrolein. The resultant methacrolein is oxidized by air in the gas phase on a heterogeneous catalyst to give methacrylic acid, which is esterified with methanol to give MMA (Ullmann's Encyclopedia of Industrial Chemistry 2012, Methacrylic Acid from Ethylene, and Trends and Future of Monomer-MMA Technologies, SUMITOMO KAGAKU 2004-II). This process has been operated since 1990 by BASF in a plant with a capacity of 40 000 metric tons per annum for methacrylic acid production. According to the SUMITOMO article, this process was developed by BASF for specific requirements, and it is therefore difficult to make general use of said process for producing larger quantities of MMA.

In a quite modern variation of this process with ethylene as starting material, the methacrolein is directly converted into MMA by an oxidative esterification in the presence of oxygen, methanol and a noble metal catalyst. Such a process can be found for example in WO 2014/170223.

Another process obtains MMA through oxidation of isobutylene or tert-butanol with atmospheric oxygen in the gas phase on a heterogeneous catalyst to give methacrolein followed by use of methanol in an oxidative esterification reaction of methacrolein. This process, developed by ASAHI, is described inter alia in the publications U.S. Pat. Nos. 5,969,178 and 7,012,039. This process is also described in the SUMITOMO article, which provides detailed information about the disadvantages of said process, consisting in particular in high energy usage, arising inter alia because of an unpressurized procedure.

In addition, other problems associated with all the processes described above are in particular the relatively unsatisfactory yield, high losses in the oxidation steps and attendant $CO_2$ formation, and in general terms the attendant formation of by-products requiring complicated steps to isolate the product: all of the processes starting from isobutylene or from equivalent C-4-based raw materials, such as TBA or MTBE, using gas-phase oxidation on a heterogeneous catalyst system achieve yields below 90%, and the relevant literature describes yields below 85% for methacrolein production starting from isobutylene (e.g. Table 5 in Ullmann's Encyclopedia/Sumitomo, see above). The gas-phase process naturally proceeds at moderate pressures of from 1 to 2 bar absolute, and produces a process gas which comprises only about 4-6% by volume of the product component. Isolation of the useful product from the inert gas ballast incurs accordingly high energy cost and consumes large amounts of cooling energy, as well as steam for multi-stage distillation work-up steps.

Production of MMA according to the methods described hitherto produces relatively large amounts of wastes, in particular exhaust gases or wastewater, which require expensive disposal.

Conduct of some of the processes described above moreover requires very complex, and therefore expensive, plant, with associated high capital expenditure and high maintenance costs.

The overview article cited above from SUMITOMO describes the respective disadvantages in detail, and can therefore be incorporated herein by way of reference.

Objectives SUMMARY OF THE INVENTION

In the light of the prior art, an objective of the present invention is therefore to provide an alternative process for producing methacrylic acid or a methacrylic acid ester which does not have the disadvantages of conventional processes.

A particular objective is to use raw materials from natural sources in this process.

Another particular objective is to enable the production of methacrylic acid or a methacrylic acid ester with a relatively low energy usage. Furthermore the process shall be carried out in a manner that provides a high level of protection of the environment, so that the quantities of wastes obtained are very small.

A further particular objective of the present invention is to develop a new process for the production of a methacrylic acid ester, especially of MMA or methacrylic acid starting from $C_3$ building blocks. Thereby it was important to improve the overall yield of methacrylic acid or a methacrylic acid ester, based on the $C_3$ raw materials used, for example by discovering and combining individual reaction steps with high product selectivity.

Moreover, it should be possible to carry out the process with a very small number of steps, which should be simple and reproducible.

In addition, it should be possible to carry out the process by using relatively simple and inexpensive plant. Capital expenditure for the plant should accordingly be small. Maintenance of this plant should be simple and inexpensive.

Other objectives not explicitly mentioned are apparent from the overall context of the description and embodiments hereinafter.

DETAILED DESCRIPTION OF THE INVENTION

A process with all of the features described below achieves the above objectives, and also achieves other objectives which are not explicitly mentioned, but which are readily derivable or deducible from the circumstances discussed in the introduction of this specification. Additional descriptions cover advantageous embodiments of the described process.

This new process for producing methacrylic acid or a methacrylic acid ester comprises the following steps:
  a) producing acrolein,
  b) reacting the acrolein of process step a) with hydrogen to produce propanal,
  c) reacting the propanal of process step b) with formaldehyde to produce methacrolein and
  d) oxidizing methacrolein in the presence of an oxygen containing gas and optionally an alcohol to methacrylic acid or a methacrylic acid ester.
Process Step a)

It is especially preferred that the acrolein of step a) is derived from a $C_3$ based raw material. In one preferred embodiment of the present invention, the acrolein is derived from propylene. In a second even more preferred embodiment acrolein is derived from glycerol.

Independent from these embodiments it is preferred to start with evaporating the $C_3$ based raw material before it is converted to acrolein in the presence of a heterogeneous contact and of a co feed gas. This feed gas comprises at least one of the components selected from hydrogen, oxygen and water.

In case the $C_3$ based raw material is propylene, this reaction is preferably carried out in a gas phase at a temperature between 300 and 400° C. It is especially preferred to make the reaction in the presence of a catalyst comprising Bismuth and Molybdenum.

In case the $C_3$ based raw material is glycerol, this glycerol is preferably evaporated and converted to acrolein in the presence of water and optionally hydrogen. It is especially preferred not to condensate the obtained acrolein, hut to convert it directly to propanal in process step h) without intermediate isolation of the acrolein.

In case in process step a) acrylic acid is formed as a byproduct, the acrolein is hydrogenated in the presence of this acrylic acid in process step b). Thereby the acrylic acid is parallel thereto at least partly hydrogenated to propionic acid. It is especially preferred to transfer this propionic acid and/or acrylic acid together with the propanal into the reactor for process step c). Here the propionic acid and/or acrylic acid act as a co catalyst for the reaction of the propanal with formaldehyde to form methacrolein. Here it is an especially preferred embodiment of the present invention where no additional acid is added to the reaction mixture of process step c) and the content of propionic acid is sufficient to efficiently carry out process step c).

In an alternative thereto the acrolein of process step a) is separated from acrylic acid by extraction and/or distillation whereby the obtained acrolein is used in process step b).
Process Step b)

In process step b) the acrolein of process step a) is reacted with hydrogen to produce propanal.

After reaction, it is especially preferred to condensate the product of process step b). Hereby a propanal containing phase is separated from a gas stream comprising hydrogen and at least two of the components water, carbon monoxide, carbon dioxide, ethane, ethylene and propane. Furthermore it is very advantageous to recycle at least a part of the gas stream by using the gas stream as a co feed in at least one of the process steps a) or b).

It is especially preferred that process step b) is carried out in the presence of a noble metal catalyst and of hydrogen.

As for the embodiment of the present invention wherein the acrolein of process step a) comprises glycerol as $C_3$ component the acrolein is hydrogenated in process step b) in the presence of hydroxyl acetone. Thereby, the hydroxyl acetone is formed as a byproduct out of acetole. As for the process following thereto, there are now two alternatives: The hydroxyl acetone is either reacted in process step d) to acetole methacrylate or in process step c) to hydroxylmethyl vinyl ketone. Itis also possible that only a part of the hydroxyl acetone is converted into acetole methacrylate and most of the residual hydroxyl acetone forms finally hydroxylmethyl vinyl ketone.

Because both of these byproducts have a negative effect like coloring on the end product, it is preferred to substantially purify intermediate acrolein of process step a) before being hydrogenated in process step b). Alternately or additionally thereto, the propanal of process step b) is substantially purified from hydroxyl acetone before being condensed in the presence of formaldehyde in process step c) is.

Thereby also further byproducts, as for example CO, CO$_2$ or H$_2$ can be separated from the raw product. In case of H$_2$, it would be preferred to recycle it.

Alternately or additionally thereto it is preferred that the intermediates of at least one of the process steps a), b) and/or c) is substantially separated from hydroxyl acetone or hydroxymethyl vinyl ketone.

In a very special embodiment of the present invention process steps a) and b) are carried out simultaneously in one reactor. It is especially surprising that by doing so the yield, the effectiveness and the selectivity of the whole process comprising steps a) to d) are still very good.

Process Step c)

The described process comprises the production of methacrolein, especially by the reaction of propanal with formaldehyde. The processes suitable for this purpose are known to the person skilled in the an and are subject matter of relevant overview articles, for example in Ullmann's Encyclopedia of 5 Industrial Chemistry 2012, Wiley-Val Verlag GmbH & Co. KGaA, Weinheim, Acrolein and Methacrolein, DOI: 10.1002/14356007.a01 149.pub2. Further, more detailed descriptions of this process can be found for example in WO 2014/170223 or in WO 2015/091173.

The reaction, which is achieved by way of an aldol condensation or Mannich condensation, is not per se critical. However, preferred processes are those which feature high yield and low by-product formation. Preferably this process step is conducted in the presence of water. It is appropriate to use reactions which have a selectivity of at least 80%, preferably at least 90% and particularly preferably at least 92%, based on the amount of propanal used.

It can also be provided that the reaction according to step c) takes place with a molar ratio of propanal to formaldehyde which is preferably in the range from 2:1 to 1:2, particularly preferably from 1.5:1 to 1:1.5. It is very particularly preferable to use an equimolar ratio of propanal to formaldehyde.

Preferred processes for producing methacrolein starting from propanal and formaldehyde are described inter alia in the publications U.S. Pat. No. 7,141,702; DE 32 13 681 A1; U.S. Pat. Nos. 4,408,079; 2,848,499; JP 4173757A (JP 19900300135); JP 3069420B2 and EP 0 317 909 A2, and for purposes related to disclosure the teaching of the said publications is hereby incorporated by way of reference into the present application.

The reaction of propanal with formaldehyde generally uses catalysts, especially inorganic acid or organic mono-, di- or polycarboxylic acid, preferably aliphatic monocarboxylic acid. Thereby, it is particularly preferable to use at least one organic acid for the reaction of propanal and formaldehyde, and even more preferably formic acid or acetic acid.

In principle, it is equally possible to use other organic acids, but they are generally less advantageous for reasons of price. Inorganic acids used are generally sulphuric acid and phosphoric acid. Acid mixtures can also be used.

The proportion of acid, based on propanal, is from 0.1 to 20 mol %, advantageously from 0.5 to 10 mol %, preferably from 1 to 5 mol %.

The reaction of propanal with formaldehyde is in most cases additionally carried out in the presence of organic bases, preferably amines, particularly preferably secondary amines.

Examples of amines that can be used are: dimethylamine, diethylamine, methylethylamine, methylpropylamine, dipropylamine, dibutylamine, diisopropylamine, diisobutylamine, methylisopropylamine, methylisobutylamine, methyl-sec-butylamine, methyl(2-methylpentyl)amine, methyl(2-ethylhexyl)amine, pyrrolidine, piperidine, morpholine, N-methylpiperazine, N-hydroxyethylpiperazine, piperazine, hexamethyleneimine, diethanolamine, methylethanolamine, methylcyclohexylamine, methylcyclopentylamine, dicyclohexylamine or appropriate mixtures.

The proportion of organic base, preferably of secondary amines, is from 0.1 to 20 mol %, advantageously from 0.5 to 10 mol %, preferably from 1 to 5 mol %, based on propanal. The ratio of the equivalents of amine to acid is preferably selected in such a way as to give a resultant pH of from 2.5 to 9 in the reaction mixture prior to the reaction.

It can also be provided that the molar ratio of acid to organic base, preferably amine, is in the range from 20:1 to 1:20, preferably in the range from 10:1 to 1:10, particularly preferably in the range from 5:1 to 1:5 and specifically preferably in the range from 2:1 to 1:2.

The reaction temperature for the reaction of propanal with formaldehyde at the exit from the reaction zone is from 100 to 300° C., preferably from 130 to 250° C., with preference from 140 to 220° C., in particular from 150 to 210° C.

The reaction pressure is in the range from 2 to 300 bar, preferably from 5 to 250 bar, particularly preferably from 10 to 200 bar, advantageously from 15 to 150 bar, preferably from 20 to 100 bar and in particular from 40 to 80 bar. Pressure and temperature are adjusted in such a way that the reaction always takes place below the boiling point of the reaction mixture, i.e. the reaction proceeds in the liquid phase. For the purposes of the present application, all pressure data are absolute pressure in the unit bar.

The residence time or reaction time is preferably at most 25 minutes, advantageously from 0.01 to 25 minutes, preferably from 0.03 to 2 minutes and specifically preferably in the range from 1 to 30 seconds. It is advantageous to use a tubular reactor as reactor at residence times below 10 minutes. The residence time here refers to the time for which the reaction mixture is reacted. All of the components are present here at reaction pressure and temperature, and the said time can therefore be calculated from the distance between the mixing point and the depressurization point. The depressurization point is the point at which the mixture is brought from reaction pressure to a pressure below 5 bar.

The reaction mixtures can also comprise, alongside water, organic solvents, e.g. propanol, dioxane, tetrahydrofuran, and methoxyethanol.

It can also be provided that the reaction of propanal with formaldehyde to give methacrolein according to step c) takes place in the presence of preferably at least 0.1% by weight, with preference at least 0.2% by weight and particularly preferably at least 0.5% by weight, of methanol, based on formaldehyde. Despite the said relatively high methanol concentrations, by virtue of the claimed conduct of the reaction for the subsequent step d) it is possible to omit any complicated removal of methanol out of the formaldehyde raw material and/or during the methacrolein purification.

According to one particular embodiment, formaldehyde and propanal can be mixed before the said starting materials are brought to reaction pressure and/or temperature.

The reaction can be carried out as follows: a mixture of propanal, amine, formaldehyde and advantageously water and/or acid and/or base is kept at the reaction temperature and the reaction pressure during the reaction time.

Step d)

According to the invention, the methacrolein obtained in step c) is oxidized in the presence of an oxygen containing gas and optionally an alcohol to methacrylic acid or a methacrylic acid ester. Thereby, process step d) is preferably an oxidative esterification of Methacrolein which is carried out in a liquid phase at a pressure from 1 to 100 bar and in the presence of a heterogeneous noble-metal-comprising catalyst. In addition it is preferred that said heterogeneous catalyst comprises a metal and/or a metal oxide.

In a first embodiment of the present invention methacrolein is oxidized to methacrylic acid. In a further step this methacrylic acid might be converted by reacting with an alcohol to a methacrylic acid alkyl ester, especially with methanol to MMA. Further details of the said process are described inter alia in Ullmann's Encyclopedia of Industrial Chemistry 2012, Wiley-VCH Verlag GmbH & Co. KGaA, Weinheim, Methacrylic Acid and Derivatives, DOI: 10.1002/14356007.a16_441.pub2, and in Trends and Future of Monomer-MMA Technologies, SUMITOMO KAGAKU 2004-II.

In the second alternative, according to this invention preferred embodiment of this process step d) methacrolein is oxidized in the presence of an alcohol. According to the invention, and alternatively the methacrolein obtained in step c) is thereby reacted in a direct oxidative esterification reaction to give a methacrylic acid ester, e.g. MMA. Details about this process step can be found for example in WO 2014/170223, WO 2015/076682, WO 2015/091173 or in WO 2015/091018.

Oxidation of methacrolein in an oxidative esterification reaction according to step d) of the process of the present invention generally produces at most 30% by weight, preferably at most 15% by weight, particularly preferably at most 5% by weight, of methacrylic acid.

An oxidative esterification reaction is carried out with an oxidant, and it is preferable to use oxygen ($O_2$) for this purpose. For reasons of cost, air can preferably be used, and can comprise different proportions of oxygen; this would not be critical for the present invention.

At least one heterogeneous oxidation catalyst is moreover used for carrying out a reaction according to step d), and these selectively accelerate the oxidation reaction defined in more detail above. Suitable catalysts are well known to persons skilled in the art and are described by way of example in the publications EP 0 857 512 A1, EP 1 393 800 A1, EP 2 177 267 A1, and EP 2 210 64 A1, and reference is made to the said publications for disclosure purposes, and the catalysts disclosed therein are incorporated into this application. Said publications also describe reaction conditions, which are likewise incorporated into the present application.

Heterogeneous oxidation catalysts preferably comprise at least one noble metal and in most cases at least one metal oxide. Preference is given here to oxidation catalysts in which gold and/or palladium and/or ruthenium and/or rhodium and/or silver is present. Gold- and/or palladium-containing catalysts are particularly preferred.

Beyond the in the publications above discussed catalysts, it is preferable to use a porous support material. The noble metal is then on the surface of these primary support particles scattered in form of secondary nano or micro particles. It is particularly preferable that the specific surface area (BET method) is generally at least 50 $m^2/g$, with preference at least 100 $m^2/g$.

It is specifically preferred that the heterogeneous oxidation catalyst comprises one or more ultra-finely dispersed metals with an average particle size of less than 20 nm selected from the group consisting of gold, palladium, ruthenium, rhodium and silver. The catalysts described above are especially preferred based on gold and/or nickel oxide and a bit less preferred palladium catalysts. Nickel-containing and gold-containing catalysts can preferably be lead-free.

The process for loading the support with the catalytically active constituents is not subject to any particular restrictions. Suitable processes are inter alia co precipitation, precipitative deposition, impregnation and vapor-phase deposition.

It can preferably be provided that the water content of the reaction mixture used for the oxidative esterification in this embodiment of step d) is preferably at most 10% by weight and with preference at most 5% by weight.

The amount of the catalyst to be used varies, depending on the composition of the feed mixture and of the catalyst, on the reaction conditions, and on the types of reaction and the like. If the catalyst used takes the form of a slurry, it is preferable that the amount used of the catalyst is from 0.01 to 0.5 kg/l of the reaction system solution.

It is also preferable that the content of methacrolein in the reaction mixture used for the oxidative esterification in step d) is at least 5% by weight, preferably at least 15% by weight and particularly preferably at least 25% by weight. It can also be provided that the oxidative esterification reaction according to step d) preferably takes place with a molar ratio of methanol to methacrolein in the range from 1:1 to 50:1, particularly preferably from 1.5:1 to 25:1 and specifically preferably from 2:1 to 10:1.

The oxidative esterification reaction can be carried out in any conventional manner, for example in a liquid-phase reaction or trickle-bed reaction. By way of example, it is possible to use any known reactor, e.g. a bubble-column reactor, a tubular reactor with air stream or a stirred reactor.

The pressure at which the said reaction is carried out can vary widely. Surprising advantages can be achieved through a reaction pressure in the range from 1 to 100 bar, preferably from 3 to 80 bar, more preferably from 4 to 50 bar and particularly preferably from 5 to 20 bar.

It is preferable to keep the reaction system at a pH of from 5 to 9, particularly from 6.5 to 8, by adding at least one basic compound preferably selected from the group consisting of an alkali metal compound and/or an alkaline earth metal compound, for example an oxide, hydroxide, carbonate, carboxylate or the like.

The oxidative esterification reaction according to second alternative step d) can take place at a temperature in the range of preferably 10° C. to 200° C., particularly preferably 40 to 150° C. and specifically preferably 60 to 120° C. and with a reaction time or residence time, which varies depending on other reaction conditions; however, it is preferably in the range from 10 minutes to 48 hours, with preference from 30 minutes to 24 hours and particularly preferably from 45 minutes to 2 hours. Further information concerning the conduct of an oxidative esterification reaction according to step d) for MMA synthesis is found inter alia in U.S. Pat. No. 4,249,019 or DE 3018071A1.

The reaction product obtained in step d) can be worked up in a known manner in order to obtain pure MMA: the reacted reaction mixture obtained through the oxidative esterification according to step d) can first be worked up by distillation, preferred with at least three distillation steps. Alternatively and/or additionally the work-up comprises at least one phase separation and/or centrifuge. Also other work-up techniques might be used in addition to the distillation steps.

It can also be provided that the reactor volume in step c) is smaller than the reactor volume in step d). The reactor volume here is based on the volumes in step c) and step d), where the starting materials used within these are reacted in the liquid phase under the elevated pressure of the respective reaction to give the products. The ratio of reactor volume in step c) to reactor volume in step d) is advantageously in the range from 1:1000 to 1:100, preferably in the range from 1:800 to 1:200 and particularly preferably in the range from 1:500 to 1:300.

Typical reactor volumes for a continuously operated production plant can by way of example be for step c) a tubular/tube-bundle reactor of capacity from 0.1 to 0.5 m$^3$ and for step d) a tubular/tube-bundle reactor of capacity from 10 to 15 m$^3$ or a continuously operated stirred tank of capacity from 50 to 100 m$^3$, but these data are not intended to represent any restriction.

It is preferable that steps a), b), c) and d) are carried out in a continuous process. Introduction of starting materials into the plant for carrying out a process according to the present invention, and removal of products from the plant, take place here continuously over any desired period. Said period can be interrupted for maintenance and repair work, however.

EXAMPLES

Synthesis of Acrolein

Example 1: Synthesis of Acrolein from Glycerol as Starting Material (Process Step a)

The following example is a reproduction of example 2 as published in WO2012/72697.

Glycerol was converted to acrolein over a catalyst bed with hydrogen used to lower the partial pressure of the reactants. A catalyst layer consisting of 56 g of a catalyst, 10 w % of WO$_3$ supported on ZrO$_2$ in grains of the size 20-30 mesh, was used. The inlet liquid stream consisted of 20 wt % of glycerol in water fed to the preheater at 0.3 g/min. A gas stream of 100 ml/min of hydrogen was also fed to the preheater. The liquid stream was preheated and vaporized, to 280° C., prior entering the reactor. The inlet of reactor was held at 300° C. and a pressure of 5 bar gauge was applied over reactor. The outlet stream was cooled down in a condenser and the water was condensed. The liquid stream was collected in a sample vessel, while the gas stream was collected in a Tedlar gas bag. The liquid sample was analyzed with a GC equipped with FID and a WAX-column for hydrocarbons (propanol, propanal, propionic acid etc.). The gas sample was analyzed with a two channel GC equipped with TCD for analyzing CO, CO$_2$, ethene, ethane etc. Glycerol was converted to beyond the detection limit and acrolein was yielded in amounts above 80%. The production of hydroxyacetone was lowered to 5% while the yields of CO and CO$_2$ essentially the same. Further, some 10% propionaldehyde was formed as a side product.

Example 2: Synthesis of Acrolein from Glycerol as Starting Material (Process Step a)

The following example is a reproduction of example 1 as published in US 2011/112330.

A Cesium salt of tungstophosphoric acid (CsPW) was used for a 20 wt % aqueous solution of glycerol in a fixed catalyst bed together with air. The fixed catalyst bed was heated at a temperature of 260° C. to 350° C. whereas the Feed gas had following composition in mol percent: glycerin:oxygen:nitrogen:water=4.2:2.2:8.1:85.5. GHSV was 2445 h$^{-1}$. Acrolein was obtained in 93.1% Yield

Example 3: Synthesis of Acrolein from Propene as Starting Material (Process Step a)

The catalyst (Mo$_1$Pd$_{01.57e-4}$Bi$_{0.09}$Co$_{0.8}$Fe$_{0.2}$Al$_{0.123}$-V$_{4.69e-3}$K$_{5.33e-3}$) was tested with a gas feed composition of nitrogen:oxygen:propylene:water in the ratio of 77:7.50:5.50:10 at 342° C., at a pressure of 15 psi, and a total flow of 130 cc/min. The reaction product showed a 99% conversion of propylene with a 98% selectivity for acrolein.

Example 4: Synthesis of Acrolein from Propene as Starting Material (Process Step a)

The following synthesis was a reproduction of example 1 in EP 1460053

A ring-shaped catalyst having the following composition Mo:Bi:Co:Fe:Na:B:K:Si:O   12:1:0.6:7:0.1:0.2:0.1:18:X (wherein X is a value determined by oxidation degrees of the respective metal elements) was used. At 200° C. a mixed reaction raw gas composed of 8 mol % of propylene, 67 mol % of air and 25 mol % of steam was fed into the reaction tubes of a fixed bed multipipe type reactor from a top thereof such that the reaction raw gas was contacted with the catalyst for 3.5 seconds. In addition, the temperature of the niter was controlled so as to attain a propylene conversion rate of 98%. The Yield of acrolein was 92.5%.

Example 5: Synthesis of Acrolein from Propane as Starting Material (Process Step a)

The following synthesis was a reproduction of example 1 in U.S. Pat. No. 6,388,129

Converting a gas mixture (modified air) consisting of 90% by volume of O$_2$ and 10% by volume of N$_2$ and 79.7 mol/h of recycled gas having the composition of 87.7% by volume of propane were converted to obtain propene via oxydehydrogenation of propane.

The by this process obtained propene can be furthermore converted to Acrolein by a process as described in example 3 or example 4.

Example 6: Synthesis of Acrolein from Allyl Alcohol as Starting Material (Process Step a)

The following synthesis was a reproduction of example 1 in US 2016/23995
Synthesis of the Catalyst with an Sb/Fe Ratio of 0.6:

A 0.05M solution was prepared by dissolving 2.21 g of oxalic acid in 500 ml of water at 80° C. with stirring. Once dissolution was complete, 140.97 g of iron nitrate nonahydrate were added to the oxalic acid solution while maintaining the temperature at 80° C. After complete dissolution of the iron nitrate nonahydrate, 30.51 g of antimony(III) oxide were added. The resulting solution was left to evaporate while maintaining the temperature at 80° C., with stirring, until a viscous solution was obtained, which was then dried in ail oven at 120° C. for 72 hours. After drying, the product obtained was pressed in the form of pellets which were subsequently ground in order to obtain a pulverulent product comprising particles having a size of between 250 and 630 μm. These particles were then calcined under static air from ambient temperature up to 500° C. while observing a temperature rise gradient of 1° C./min and then a phase of maintenance at 500° C. for 8 hours. The catalyst was subsequently left in the oven until the temperature had returned to 50° C. A catalyst exhibiting an Sb/Fe ratio of 0.6 (i.e., x=0.6) was obtained.

5 g of the catalyst prepared were placed in a fixed bed reactor. The reaction was carried out with a 7.2% by weight aqueous allyl alcohol solution. The reactor was heated to 400° C. and then fed with reactants (allyl alcohol/O2/NH$_3$) at atmospheric pressure. The contact time of the reactants with the catalyst was of the order of 0.1 sec. The reaction time was 5 hours. The products resulting from the reaction were analyzed after trapping at the reactor outlet in a bubbler maintained at low temperature (−4° C.). The liquid obtained was subsequently analyzed on a gas chromatograph equipped with a flame ionization detector. Allyl alcohol/O2/NH3 molar ratio: 1/1.6/0.4: Conversion of the allyl alcohol 87%, Yield: 17% Acrylonitrile, 52% acrolein, 5% acetaldehyde, 5% propionaldehyde, 1% acetonitrile.

Example 7: Synthesis of Acrolein from Acetol as Starting Material (Process Step a)

The following synthesis was a reproduction of example 7 in US 2016/23995
Dehydration of Acetol to Acrolein via activated carbon and phosphoric acid at 290° C. with full conversion of Acetol and selectivity of >55% for Acrolein.

Example 8: Synthesis of Propionaldehyde from Acrolein as Starting Material (Process Step b)

The following synthesis was a reproduction of example 1 in DE 755524 The experiments were run at an aldehyde-to-hydrogen ratio of 1:2 on a molar basis and at 5 bar operating pressure. An aqueous solution of 10 wt % acrolein and hydrogen was fed to a preheater, wherein the mixture was heated to about 150° C. The resulting mixed gaseous stream was then fed to a reactor comprising the catalyst (2 wt % Pd on Al$_2$O$_3$— and one where the Pd has been concentrated to the outermost surface of the catalyst (0.18 wt % Pd on Al$_2$O$_3$)). Full conversion of acrolein was observed. The selectivity to propionaldehyde was about 85%. Side products hydroxyacetone, CO and CO$_2$.

Example 9: Synthesis of Methacrolein (MAL) from Propionaldehyde and Formaldehyde as Starting Materials (Process Step c)

Propionaldehyde (PA) is reacted continuously with formaldehyde with use of dimethylamine (DMA) and acetic acid (AcOH). 251 g/h of PA and 349 g/h of a 37 percent formalin solution are premixed homogeneously (molar ratio 1:1). 18.7 g/h of a catalyst solution with 24.8% of dimethylamine and 37.9% of acetic acid are passed into the preheater 12. The two streams are heated to a temperature of 170'C before they are combined. The preheated streams are combined in a T mixer which has direct connection to a tubular reactor (1/16 inch tube, length 4.2 m). The temperature of the reactor is controlled by an oil bath operated at 180° C., residence time is 10 s, and the pressure in the tubular reactor is 70 bar. Downstream of the tubular reactor, the mixture is depressurized in valve (14) and is introduced into the column (15). 335 g/h of the material discharged at the bottom of the column are returned to the reactor (13), and 370 g/h of the material discharged at the bottom of the column are passed for disposal in the form of wastewater. After condensation of the overhead stream in the condenser (16) and phase separation in (17), a methacrolein-rich phase with 96.5% methacrolein content is discharged as product (111), and the aqueous material discharged from the phase separator is returned to the column (15). Conversion is 99.9% and yield is 98.1%, based on propionaldehyde.

Example 10: Synthesis of MMA or Methacrylic Acid from Methacrolein as Starting Material (Process Step d)

Catalyst carrier synthesis: In a beaker 21.36 g Mg(NO3)2*6H20, 31.21 g Al(NO$_3$)$_3$*9H$_2$0 are dissolved by stirring in 41.85 g water. 1.57 g 60% ige HNO3 were added while stirring. 166.67 g Silicasol (Köstrosol 1530AS, 30 w % SiO$_2$, particle size: 15 nm) are placed in a 500 ml three necked flask and cooled to 15° C. while stirring. 2.57 g 60% ige HNO$_3$ were added slowly to this under vigorous stirring. At 15° C. the nitrate solution prepared before is added within 45 min to the Sol. On complete addition the mixture is heated within 30 min to 50° C. and aged for 24 h (while stirring) at this temperature. Afterwards this mixture is spray dried at 130° C. The dried powder, (spherical, average particle size 60 μm) is heated in thin layers within 2 h to 300° C. Kept for 3 h at 300° C., heated within 2 h to 600° C. and kept here for 3 h. Metal impregnation of catalyst carrier: A suspension of 10 g carrier prepared before is mixed with 33.3 g water and heated to 90° C. Is kept 15 min at this temperature, subsequently a 90° C. preheated solution of Co(NO$_3$)2*6H$_2$0 (569 mg, 1.95 mmol) in 8.3 g water is added and the mixture is stirred afterwards for 30 min at 90° C. After cooling to room temperature the mixture is filtered and washed six times with each 50 mL water. The material was dried 10 h at 105° C. and carefully grinded afterwards. Finally the material is heated within 1 h from 18 to 450° C. to be kept at this temperature for 5 h.

Nobel metal impregnation of metal catalyst: 10 g of the Cobalt catalyst prepared before are heated in 33.3 g water to 90° C. and kept at this temperature, while stirring, for 15 min. A 90° C. preheated solution of HAuCl$_4$*3H$_2$0 (205 mg) in 8.3 g water was added slowly the mixture was after stirred 30 min at 90° C. on complete addition and is finally cooled to room temperature. The materials is isolated by filtration and washed six times with each 50 mL water. The material was dried 10 h at 105° C., carefully mortared and finally calcined for 5 h at 450° C. calcined.

Continuous conversion of Methacrolein to MMA/MAS: The pH-Value of a feed containing 42.5 w % solution of Methacrolein in MMA is adjusted to 7 by addition of a solution of NaOH in MeOH. The feed is added continuously to a stirred and gasified (with air) tank reactor at 10 bar pressure and 80° C. The reactor was charged before with 20 g Gold-Cobalt catalyst as prepared before. Additionally to the feed of MeOH and Methacrolein a second feed with 1 w % NaOH in MeOH is continuously added to the reactor to keep the pH at 7.0. The reactor was operated at constant volume level and excess of volume was continuously removed via a filter, to keep the catalyst inside the reactor. After 2000 h TOS the catalyst had still a conversion of 73.8% Methacrolein at a selectivity of 95.5% to MMA. Methacrylic acid is made additionally with a selectivity of 1%.

Example 11: Synthesis of MMA or Methacrylic Acid from Methacrolein as Starting Material (Process Step d)

In this example a catalyst containing Ni and Au was used.
Catalyst carrier synthesis: In a beaker 21.36 g Mg(NO$_3$)$_2$*6 H$_2$O, 31.21 g Al(NO3)3*9 H$_2$0 are dissolved by stirring in 41.85 g water. 1.57 g 60% HNO$_3$ were added while stirring. 166.67 g Silicasol (Köstrosol 1530AS, 30 w % $SiO_2$, particle size: 15 nm) are placed in a 500 mL three necked flask and cooled to 15° C. while stirring. 2.57 g 60% $HNO_3$ were added slowly to this under vigorous stirring. At 15° C. the nitrate solution prepared before is added within 45 min to the solution. On complete addition the mixture is heated within 30 min to 50° C. and aged for 24 h (while stirring) at this temperature. Afterwards this mixture is spray dried at 130° C. The dried powder, (spherical particles with an average particle size of 60 μm) is heated in thin layers within 2 h to 300° C., kept for 3 h at 300'C, heated within 2 h to 600° C. and finally kept at this temperature for additional 3 h.

Metal & nobel metal impregnation of catalyst carrier: A suspension of 10 g carrier prepared before is mixed with 33.3 g water and heated to 90° C. It is kept for 15 min at this temperature, subsequently a 90° C. preheated solution of $HAuCl_4$*3 $H_2O$ (205 mg) and $Ni(NO_3)_2$*6 $H_2O$ (567 mg, 1.95 mmol) in 8.3 g water is added and the mixture is stirred afterwards for 30 min at 90° C. After cooling to room temperature #the mixture is filtered and washed six times with each 50 mL water. The resulting material was dried 10 h at 105° C. and carefully grinded afterwards. Finally the material is heated within 1 h from 18 to 450° C. to be kept at this temperature for 5 h.

Continuous conversion of Methacrolein to MMA/MAS: The pH-Value of a feed containing 42.5 wt % solution of methacrolein in MMA is adjusted to 7 by addition of a solution of NaOH in MeOH. The feed is added continuously to a stirred and gasified (with air) tank reactor at 10 bar pressure and 80° C. The reactor was charged before with 20 g Gold-Nickel-catalyst as prepared before. Additionally to the feed of MeOH and Methacrolein a second feed with 1 wt % NaOH in MeOH is continuously added to the reactor to keep the pH at 7.0. The reactor was operated at constant volume level and excess of volume was continuously removed via a filter, to keep the catalyst inside the reactor. After 2000 h TOS the catalyst had still a conversion of 73.8 wt % Methacrolein at a selectivity of 95.5% to MMA. Methacrylic acid is made additionally with a selectivity of 1%.

Example 12: Synthesis of MMA or Methacrylic Acid from Methacrolein as Starting Material (Process Step d)

In this example a catalyst containing Pd and Pb was used. The synthesis is based on example 1 as disclosed in U.S. Pat. No. 6,680,405.

In a 4 L reactor equipped with a condenser and a stirrer, 350 g of a catalyst (a calcium carbonate catalyst containing 5 wt % palladium, 1 wt % lead and 1 wt % iron) and a reaction liquid of 700 g of methacrolein and 1280 g of methanol were charged. The reaction was continued for 4 hours at a bath temperature of 80° C. and under pressure of 400 kPa*abs, while blowing air and nitrogen at rates of 4.77 Nl/min and 5.0 Nl/min, respectively, thereby to synthesize methyl methacrylate. The reaction product was collected and analyzed, and as a result, a conversion of methacrolein and a selectivity of methyl methacrylate were found to be 75.1% and 85.2%, respectively.

Example 13: Synthesis of MMA or Methacrylic Acid from Methacrolein as Starting Material (Process Step d)

In this example a catalyst containing Pd and Pb was used. The synthesis is based on example 1 as disclosed in US 2014/206897.

50.1 g of methacrolein is added to the reactor, along with 25.2 g of methanol (for a molar ratio of methanol to methacrolein of about 1.1). Roughly 1 g of catalyst (e.g. comprising 3 wt % palladium and 2 wt % lead on silica) is added to the solution. A stirrer is turned on, and the solution is heated to about 50° C. Oxygen flow is begun at about 6 milliliters per minute (mL/min). The reactor is open to atmospheric pressure. The reaction is continued for about 4 hours. This results in methacrolein conversion of about 50 percent, with selectivity to methyl methacrylate of about 90 percent.

Example 14: Oxidation of Methacrolein to Methacrylic Acid in the Gas Phase (Process Step d)

Preparation of aqueous slurry A1: In 105 g of ion-exchange water heated to 40° C., 38.2 g of cesium nitrate [$CsNO_3$], 12.8 g of 75 wt % orthophosphoric acid, and 12.2 g of 67.5 wt % nitric acid were dissolved to form a liquid α. Separately, 138 g of ammonium molybdate tetrahydrate [$(NH_4)_6Mo_7O_{24}$. $4H_2O$] was dissolved in 154 g of ion-exchange water heated to 40° C., followed by suspending 3.82 g of ammonium metavanadate [$NH_4VO_3$] therein to form liquid β. Liquid α was dropwise added to Liquid β while stirring and maintaining the temperatures of liquids α and β at 40° C. to obtain aqueous slurry A1. The atomic ratios of metal elements, i.e., phosphorus, molybdenum, vanadium and cesium contained in aqueous slurry A1 were 1.5, 12, 0.5 and 3.0, respectively, and thus the atomic ratio of cesium to molybdenum was 3.0:12.

Preparation of aqueous slurry B1: In 120 g of ion-exchange water heated to 40° C., 14.6 g of 75 wt % orthophosphoric acid and 13.9 g of 67.5 wt % nitric acid were dissolved to form liquid α. Separately, 158.2 g of ammonium molybdate tetrahydrate was dissolved in 176 g of ion-exchange water heated to 40° C., followed by suspending 4.37 g of ammonium metavanadate therein to form liquid b. Liquid α was dropwise added to liquid b while stirring and maintaining the temperatures of liquids α and b at 40° C. to obtain aqueous Slurry B1. The atomic ratios of the metal elements, i.e., phosphorus, molybdenum and vanadium contained in aqueous slurry B1 were 1.5, 12 and 0.5, respectively, and thus the atomic ratio of cesium to molybdenum was 0:12.

Preparation of aqueous slurry M1: The whole quantity of aqueous slurry B1 was mixed with the whole quantity of aqueous slurry A1, and then the mixture was stirred in a closed vessel at 120° C. for 5 hours. Then, to the mixture, the suspension of 10.2 g of antimony trioxide [$Sb_2O_3$] and 10.1 g of copper nitrate trihydrate [$Cu(NO_3)_2$, $3H_2O$] in 23.4 g of ion-exchange water was added, and the mixture was further stirred in the closed vessel at 120° C. for 5 hours to obtain aqueous slurry M1. The aqueous slurry M1 was dried by heating it in an air at 135° C. to evaporate water therefrom. To 100 parts by weight of the dried product, 4 parts by weight of ceramic fiber, 17 parts by weight of ammonium nitrate and 7.5 parts by weight of ion-exchange water were added, and the mixture was kneaded and extrusion-molded into cylinders each having a diameter of 5 mm and a height of 6 mm. The molded cylinders were dried at 90° C. and a relative humidity of 30% for 3 hours and then calcined by maintaining them in an air stream at 390° C. for 4 hours and then in a nitrogen stream at 435° C. for 4 hours to obtain the catalyst. The catalyst comprised a heteropolyacid compound, and the atomic ratios of the metal elements other than oxygen, i.e., phosphorus, molybdenum, vanadium, antimony, copper and cesium contained in the heteropolyacid compound were 1.5:12:0.5:0.5:0.3:1.4, respectively, and thus the atomic ratio of cesium to molybdenum was 1.4:12.

9 g of the catalyst, synthesized as described before were charged into a glass micro-reactor having an inner diameter of 16 mm, and a starting gas composed of 4 vol % of methacrolein, 12 vol % of molecular oxygen, 17 vol % of water vapor and 67 vol % of nitrogen, prepared by mixing methacrolein, air, steam and nitrogen, was fed to the reactor at a space velocity of 670 $h^{-1}$, and a reaction was carried out at a furnace temperature (the temperature of a furnace used for heating the micro-reactor) of 355° C. for one hour. Then, the starting gas having the same composition as above was fed to the micro-reactor at the same space velocity as above, and the reaction was re-started at a furnace temperature of 280° C. After carrying out the reaction for 1 hour from the re-start of the reaction, an exit gas (a gas after reaction) was sampled and analyzed by gas chromatography, and a conversion of methacrolein (percent), a selectivity of 80% to methacrylic acid (percent) and a yield of 77% methacrylic acid were obtained at 96% conversion.

Example 16: Direct Conversion of Glycerol to Propionaldehyde without Condensation Crude glycerol (containing water, comprising salts (mainly NaCl and KCl) was converted to acrolein over a catalyst bed with hydrogen used to lower the partial pressure of the reactants. A catalyst layer consisting of 56 g of a catalyst, 10 wt % of $WO_3$ supported on $ZrO_2$ in grains of the size between 20 and 30 mesh, was used. The inlet liquid stream consisted of 20 wt % of crude glycerol in water fed to the preheater at 0.3 g/min. A gas stream containing at least 100 ml/min of hydrogen was also fed to the preheater. The liquid stream was preheated and vaporized, to a temperature between 250 and 300° C. (ideal 280° C.), prior entering the reactor. The inlet of reactor was held at 275 to 325° C. (ideal 300° C.) and a pressure in the range between 1 and 5 bar gauge was applied over reactor. The outlet stream consist on a large amount of acrolein with side product propionaldehyde (propanal) and acetol (beside the majority of water) and was further cooled (but not condensed) to a temperature in the range between 130 and 200° C. (ideal 170 to 180° C.). The stream was fed directly to the second reactor comprising an egg shell catalyst (2 wt % Pd on $Al_2O_3$). The stream leaving the reactor consist did not contain any glycerol or acrolein. The stream was cooled to condensate water and propionaldehyde and subsequently the pressure was decreased to 0 to 3 bar gauge. By this a liquid and a gaseous stream was obtained. The gaseous stream was spitted into a purge (1 to 20 vol % of total volume)—which was discarded—and a recycle stream which was used as hydrogen feed for the first reactor. The Gaseous feed consists typically of 26 wt % propionaldehyde, 1 wt % $H_2O$, 21 wt % $H_2$ and 52 wt % CO and was mixed with a second gaseous feed from the Propionaldehyde distillation, which typically consist of 55 wt % propionaldehyde, 1 wt % $H_2O$, 4 wt % $H_2$, 1.5 wt % CO, 23 wt % ethane and 2 wt % ethene. The obtained gas stream was enriched with pure hydrogen to meet the requirements as a hydrogen feed for the first reactor. Surprisingly no components in this feed had measurable negative influence on the performance of the first two steps. The liquid stream obtained before (together with the gaseous stream) consist typically of 12.1 wt % oropionaldehyd, 87.5 wt % water and 0.2 wt % acetol. Beside this some dissolved gasses, like 0.2 wt % ethane and ethene are present. The liquid is fed to the lower third of a distillation column to separate propionaldehyde as head product in 96.5% purity beside 2.7% of water and the dissolved gases, which are separated by cooling the mixture to condensate Propionaldehyde and water as final product. The gaseous stream is combines, as described earlier. The water leaving the column as bottom product, contains mainly water and high boiling side products like acetol. Surprisingly, this stream cannot be used as water feed for the first reactor and has to be discarded. The propionaldehyde obtained by this, is converted to methacrolein in the next step.

The invention claimed is:

1. A process for producing methacrylic acid or a methacrylic acid ester, the process comprising:
   a) producing acrolein from a raw material comprising propylene,
   b) reacting the acrolein of a) with hydrogen to produce propanal,
   c) reacting the propanal of b) with formaldehyde to produce methacrolein,
   d) oxidizing the methacrolein in the presence of an oxygen containing gas and optionally an alcohol, to the methacrylic acid or the methacrylic acid ester, and
   wherein the acrolein of a) is hydrogenated in the presence of acrylic acid, which is formed in a) as a byproduct, and wherein the acrylic acid is hydrogenated to propionic acid in b).

2. The process according to claim 1, wherein the acrolein of a) is produced from oxidation of the propylene in gas phase, at a temperature between 300 and 400° C., in the presence of a catalyst comprising bismuth and molybdenum.

3. A process for producing methacrylic acid or a methacrylic acid ester, the process comprising:
   a) producing acrolein from a raw material comprising propylene,
   b) reacting the acrolein of a) with hydrogen to produce propanal,
   c) reacting the propanal of b) with formaldehyde to produce methacrolein, and
   d) oxidizing the methacrolein in the presence of an oxygen containing gas and optionally an alcohol, to the methacrylic acid or the methacrylic acid ester,
   wherein acrylic acid, which is formed in a) as a byproduct and/or propionic acid, which is formed in b) from hydrogenation of the acrylic acid in step b) reacts as a co-catalyst in c).

4. The process according to claim 1, wherein the propylene of a) is evaporated and thereafter converted in the presence of a heterogeneous contact and a co-feed gas comprising at least one component selected from the group consisting of hydrogen, oxygen, and water.

5. The process according to claim 1, wherein a product of b) is condensed and separated from a gas stream comprising hydrogen and at least two components selected from the group consisting of water, carbon monoxide, carbon dioxide, ethane, ethylene, and propane; and
   wherein at least a part of the gas stream is recycled by using the gas stream as a co-feed in at least one of a) or b).

6. The process according to claim 1, wherein c) is carried out in the presence of from 0.1 to 20 mol % of an organic base, and in the presence of from 0.1 to 20 mol % of an acid, based in each case on the propanal.

7. The process according to claim 1, wherein d) is an oxidative esterification of methacrolein, which is carried out in a liquid phase at a pressure of from 1 to 100 bar, and in the presence of a heterogeneous noble-metal-comprising catalyst comprising a metal and/or a metal oxide.

8. The process according to claim 7, wherein the catalyst comprises one or more ultra-finely dispersed metals with an average particle size of less than 20 nm selected from the group consisting of gold, palladium, ruthenium, rhodium, and silver.

9. A process for producing methacrylic acid or a methacrylic acid ester, the process comprising:
   a) producing acrolein from a raw material comprising propylene,
   b) reacting the acrolein of a) with hydrogen to produce propanal,
   c) reacting the propanal of b) with formaldehyde to produce methacrolein, and
   d) oxidizing the methacrolein in the presence of an oxygen containing gas and optionally an alcohol, to the methacrylic acid or the methacrylic acid ester,
   wherein a) and b) are carried out simultaneously in one reactor.

10. The process according to claim 1, wherein b) is carried out in the presence of a noble metal catalyst and hydrogen.

11. The process according to claim 6, wherein the organic base is a secondary amine.

12. The process according to claim 6, wherein the acid is an organic acid.

13. The process according to claim 6, wherein a molar ratio of the acid to the organic base ranges from 20:1 to 1:20.

14. The process according to claim 3, wherein c) is carried out in the presence of from 0.1 to 20 mol % of an organic base, and in the presence of from 0.1 to 20 mol % of an acid, based in each case on the propanal.

15. The process according to claim 9, wherein c) is carried out in the presence of from 0.1 to 20 mol % of an organic base, and in the presence of from 0.1 to 20 mol % of an acid, based in each case on the propanal.

16. The process according to claim 3, wherein b) is carried out in the presence of a noble metal catalyst and hydrogen.

17. The process according to claim 9, wherein b) is carried out in the presence of a noble metal catalyst and hydrogen.

18. The process according to claim 3, wherein d) is an oxidative esterification of methacrolein, which is carried out in a liquid phase at a pressure of from 1 to 100 bar, and in the presence of a heterogeneous noble-metal-comprising catalyst comprising a metal and/or a metal oxide.

19. The process according to claim 9, wherein d) is an oxidative esterification of methacrolein, which is carried out in a liquid phase at a pressure of from 1 to 100 bar, and in the presence of a heterogeneous noble-metal-comprising catalyst comprising a metal and/or a metal oxide.

* * * * *